United States Patent
Webler (10) Patent No.: US 6,450,964 B1
(45) Date of Patent: Sep. 17, 2002

(54) IMAGING APPARATUS AND METHOD

(75) Inventor: William E. Webler, Newark, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 21 days.

(21) Appl. No.: 09/655,768

(22) Filed: Sep. 5, 2000

(51) Int. Cl.$^7$ ................................................. A61B 8/14
(52) U.S. Cl. ........................................................ 600/467
(58) Field of Search ............................... 600/459, 460, 600/461, 463, 468, 437, 467, 464

(56) References Cited

U.S. PATENT DOCUMENTS

| | | |
|---|---|---|
| 4,887,605 A | 12/1989 | Angelsen et al. |
| 5,115,814 A | 5/1992 | Griffith et al. |
| 5,193,546 A | 3/1993 | Shakhovich et al. |
| 5,243,988 A | 9/1993 | Sieben et al. |
| 5,321,501 A | 6/1994 | Swanson et al. |
| 5,459,570 A | 10/1995 | Swanson et al. |
| 5,485,845 A * | 1/1996 | Verdonk et al. ............. 600/461 |
| 5,817,021 A | 10/1998 | Reichenberger |
| 5,817,092 A | 10/1998 | Behl |
| 5,921,934 A * | 7/1999 | Teo ............................. 600/468 |
| 6,019,726 A * | 2/2000 | Webb .......................... 600/459 |
| 6,165,127 A * | 12/2000 | Crowley ....................... 600/463 |

OTHER PUBLICATIONS

Harm ten Hoff, Scanning Mechanisms For Intravascular Ultrasound Imaging: a flexible approach, Printing and binding: universiteitsdrukkerij Erasmus Universiteit Rotterdam, CIP–DATA Koninklijke Bibliotheek, Den Haag, Thesis Rotterdam–with ref ISBN 90–9006072–3, NUGI 743, headings: Intravascular ultrasound imaging/catheters, Copyright 1993, The Netherlands.

* cited by examiner

*Primary Examiner*—Francis J. Jaworski
*Assistant Examiner*—Manlin Patel
(74) *Attorney, Agent, or Firm*—Blakely, Sokoloff, Taylor & Zafman LLP (57) ABSTRACT

An apparatus and method for determining angular position of a sensor within a catheter. The invention is particularly useful for imaging devices delivered to a body lumen by a catheter, as may be the case for IVUS imaging catheters. The apparatus consists of a catheter having an inner core with an imaging sensor disposed within an inner diameter of a sheath of the catheter. The sheath is also provided with an outer diameter which has a center which it does not share with a center of the inner diameter. As a result, the catheter has a wall of non-uniform thickness. The imaging sensor is able to determine its position within its imaging rotation due to the non-uniform thickness. This positioning characteristic helps eliminate any Non-Uniform Rotational Distortion (NURD), which would otherwise result in undesired and unpredictable compressed and expanded images of vasculature sought to be imaged. A method is provided whereby the non-uniform thickness of the wall can be used to locate sensor position angularly within 0.1 degree of accuracy.

32 Claims, 6 Drawing Sheets

| Nominal | | | | h at High End of Tolerance | | | | h at Low End of Tolerance | | |
|---|---|---|---|---|---|---|---|---|---|---|
| $R_1$(in.)= | 0.0165 | | | $R_1$(in.)= | 0.0165 | | | $R_1$(in.)= | 0.0165 | |
| $R_2$(in.)= | 0.0225 | | | $R_2$(in.)= | 0.0225 | | | $R_2$(in.)= | 0.0225 | |
| h(in.)= | 0.0020 | | | h(in.)= | 0.0030 | | | h(in.)= | 0.0010 | |
| $d_{max}$(in.)= | 0.0060 | | | $d_{max}$(in.)= | 0.0090 | | | $d_{max}$(in.)= | 0.0070 | |
| $d_{min}$(in.)= | 0.0040 | | | $d_{min}$(in.)= | 0.0030 | | | $d_{min}$(in.)= | 0.0050 | |
| Angle "A" Degrees | $\cos^2$(A) | Std. Dev. | Std. Error Degrees | Angle "A" Degrees | $\cos^2$(A) | Std. Dev. | Std. Error Degrees | Angle "A" Degrees | $\cos^2$(A) | Std. Dev. | Std. Error Degrees |
| 0 | 1.0000 | 0.00E+00 | 0.000 | 0 | 1.0000 | 0.00E+00 | 0.000 | 0 | 1.0000 | 0.00E+00 | 0.000 |
| 10 | 0.9835 | 6.71E-04 | 0.205 | 10 | 0.9828 | 5.16E-05 | 0.015 | 10 | 0.9841 | 1.72E-05 | 0.005 |
| 20 | 0.9345 | 2.61E-03 | 0.405 | 20 | 0.9319 | 2.01E-04 | 0.030 | 20 | 0.9371 | 6.67E-05 | 0.011 |
| 30 | 0.8549 | 5.57E-03 | 0.597 | 30 | 0.8493 | 4.29E-04 | 0.044 | 30 | 0.8605 | 1.43E-04 | 0.016 |
| 40 | 0.7477 | 9.22E-03 | 0.774 | 40 | 0.7384 | 7.11E-04 | 0.058 | 40 | 0.7569 | 2.36E-04 | 0.020 |
| 50 | 0.6167 | 1.31E-02 | 0.933 | 50 | 0.6036 | 1.01E-03 | 0.070 | 50 | 0.6297 | 3.35E-04 | 0.024 |
| 60 | 0.4666 | 1.68E-02 | 1.069 | 60 | 0.4498 | 1.30E-03 | 0.081 | 60 | 0.4833 | 4.28E-04 | 0.028 |
| 70 | 0.3027 | 1.98E-02 | 1.176 | 70 | 0.2829 | 1.53E-03 | 0.090 | 70 | 0.3224 | 5.04E-04 | 0.030 |
| 80 | 0.1305 | 2.17E-02 | 1.251 | 80 | 0.1087 | 1.68E-03 | 0.096 | 80 | 0.1521 | 5.54E-04 | 0.032 |
| 90 | -0.0445 | 2.24E-02 | 1.290 | 90 | -0.0670 | 1.73E-03 | 0.100 | 90 | -0.0222 | 5.71E-04 | 0.033 |
| 100 | -0.2168 | 2.17E-02 | 1.290 | 100 | -0.2386 | 1.68E-03 | 0.101 | 100 | -0.1952 | 5.54E-04 | 0.033 |
| 110 | -0.3813 | 1.98E-02 | 1.249 | 110 | -0.4011 | 1.53E-03 | 0.098 | 110 | -0.3617 | 5.04E-04 | 0.031 |
| 120 | -0.5334 | 1.68E-02 | 1.167 | 120 | -0.5502 | 1.30E-03 | 0.092 | 120 | -0.5167 | 4.28E-04 | 0.029 |
| 130 | -0.6689 | 1.31E-02 | 1.045 | 130 | -0.6820 | 1.01E-03 | 0.083 | 130 | -0.6558 | 3.35E-04 | 0.026 |
| 140 | -0.7844 | 9.22E-03 | 0.886 | 140 | -0.7936 | 7.11E-04 | 0.071 | 140 | -0.7752 | 2.36E-04 | 0.022 |
| 150 | -0.8771 | 5.57E-03 | 0.695 | 150 | -0.8827 | 4.29E-04 | 0.056 | 150 | -0.8716 | 1.43E-04 | 0.017 |
| 160 | -0.9449 | 2.61E-03 | 0.478 | 160 | -0.9475 | 2.01E-04 | 0.039 | 160 | -0.9423 | 6.67E-05 | 0.012 |
| 170 | -0.9861 | 6.71E-04 | 0.244 | 170 | -0.9868 | 5.16E-05 | 0.020 | 170 | -0.9855 | 1.72E-05 | 0.006 |
| 180 | -1.0000 | 0.00E+00 | 0.000 | 180 | -1.0000 | 0.00E+00 | 0.000 | 180 | -1.0000 | 0.00E+00 | 0.000 |
| 190 | -0.9861 | 6.71E-04 | 0.244 | 190 | -0.9868 | 5.16E-05 | 0.020 | 190 | -0.9855 | 1.72E-05 | 0.006 |
| 200 | -0.9449 | 2.61E-03 | 0.478 | 200 | -0.9475 | 2.01E-04 | 0.039 | 200 | -0.9423 | 6.67E-05 | 0.012 |
| 210 | -0.8771 | 5.57E-03 | 0.695 | 210 | -0.8827 | 4.29E-04 | 0.056 | 210 | -0.8716 | 1.43E-04 | 0.017 |
| 220 | -0.7844 | 9.22E-03 | 0.886 | 220 | -0.7936 | 7.11E-04 | 0.071 | 220 | -0.7752 | 2.36E-04 | 0.022 |
| 230 | -0.6689 | 1.31E-02 | 1.045 | 230 | -0.6820 | 1.01E-03 | 0.083 | 230 | -0.6558 | 3.35E-04 | 0.026 |
| 240 | -0.5334 | 1.68E-02 | 1.167 | 240 | -0.5502 | 1.30E-03 | 0.092 | 240 | -0.5167 | 4.28E-04 | 0.029 |
| 250 | -0.3813 | 1.98E-02 | 1.249 | 250 | -0.4011 | 1.53E-03 | 0.098 | 250 | -0.3617 | 5.04E-04 | 0.031 |
| 260 | -0.2168 | 2.17E-02 | 1.290 | 260 | -0.2386 | 1.68E-03 | 0.101 | 260 | -0.1952 | 5.54E-04 | 0.033 |
| 270 | -0.0445 | 2.24E-02 | 1.290 | 270 | -0.0670 | 1.73E-03 | 0.100 | 270 | -0.0222 | 5.71E-04 | 0.033 |
| 280 | 0.1305 | 2.17E-02 | 1.251 | 280 | 0.1087 | 1.68E-03 | 0.096 | 280 | 0.1521 | 5.54E-04 | 0.032 |
| 290 | 0.3027 | 1.98E-02 | 1.176 | 290 | 0.2829 | 1.53E-03 | 0.090 | 290 | 0.3224 | 5.04E-04 | 0.030 |
| 300 | 0.4666 | 1.68E-02 | 1.069 | 300 | 0.4498 | 1.30E-03 | 0.081 | 300 | 0.4833 | 4.28E-04 | 0.028 |
| 310 | 0.6167 | 1.31E-02 | 0.933 | 310 | 0.6036 | 1.01E-03 | 0.070 | 310 | 0.6297 | 3.35E-04 | 0.024 |
| 320 | 0.7477 | 9.22E-03 | 0.774 | 320 | 0.7384 | 7.11E-04 | 0.058 | 320 | 0.7569 | 2.36E-04 | 0.020 |
| 330 | 0.8549 | 5.57E-03 | 0.597 | 330 | 0.8493 | 4.29E-04 | 0.044 | 330 | 0.8605 | 1.43E-04 | 0.016 |
| 340 | 0.9345 | 2.61E-03 | 0.405 | 340 | 0.9319 | 2.01E-04 | 0.030 | 340 | 0.9371 | 6.67E-05 | 0.011 |
| 350 | 0.9835 | 6.71E-04 | 0.205 | 350 | 0.9828 | 5.16E-05 | 0.015 | 350 | 0.9841 | 1.72E-05 | 0.005 |
| 360 | 1.0000 | 0.00E+00 | 0.000 | 360 | 1.0000 | 0.00E+00 | 0.000 | 360 | 1.0000 | 0.00E+00 | 0.000 |

FIG. 6

IMAGING APPARATUS AND METHOD

BACKGROUND OF THE INVENTION

The present invention relates to intravascular imaging catheters. In particular, intravascular catheters, such as intravascular ultrasound (IVUS) catheters, which utilize a transducer mounted on a rotating core within a stationary sheath.

BACKGROUND OF THE PRIOR ART

Ultrasonic catheter imaging systems have been developed to provide cross-sectional structural images of blood vessels, normally coronary arteries. For example, a fluid filled sheath surrounding an ultrasonic transducer subassembly at the distal end of an imaging core may be used to accomplish such imaging. The sheath is positioned within a blood vessel at the site of interest (i.e. the location of a stenosis). The transducer generates a series of sonic pulses which are transmitted outward from the transducer subassembly as it is rotated. Echo pulses reflected from the surrounding tissues are received by the transducer subassembly and collected by a control apparatus coupled to the proximal end of the sheath. The collected data is then displayed as a cross-sectional ultrasonic image of the vessel and surrounding tissue.

A transducer subassembly is generally rotated by a control apparatus at an approximate rate of 1800 Revolutions Per Minute (RPM) within the sheath. Like sonar, the transducer, periodically emits a sonic pulse through the sheath. Echoes of the transmitted pulse are returned from the surrounding tissues (including the blood vessel wall of interest). The echoes travel through the fluid filled sheath to the transducer subassembly and are eventually collected by the control apparatus which forms the ultrasonic image of the blood vessel and surrounding tissue.

A transducer subassembly is located within the apparatus near the distal end of a long thin imaging core assembly. The assembly may be made of a duplex spring originating proximally at a control apparatus and surrounding a coaxial cable. The core provides communication between the control apparatus and the transducer subassembly. The control apparatus rotates the proximal end of the core at a constant rate, typically 1800 RPM. The control apparatus excites the transducer subassembly to generate an ultrasonic pulse at equal intervals of rotation, typically every 1.5° or less. Thus, approximately 240 or more cycles of image data (i.e. transmissions and echoes) are generated and collected by the control apparatus as the proximal end of the core makes each 360° rotation. This equates to image data collection occurring approximately every 0.14 milliseconds. The collected data is used to create the cross-sectional image of the vessel and surrounding tissue.

While the control apparatus directs a constant rate of rotation at the proximal end of the core, the distal end of the core is only guaranteed to rotate at an average rate equivalent to that of the proximal end of the core. The rotation rate of the distal end will not be constant. Rather, the rate will fluctuate within each rotation. This varying rotational rate of the distal end of the core is due to flexural and dimensional non-uniformities of the core. The rotation rate of the distal end of the core will both increase and decrease within each rotation. This effect is generally referred to as "whipping". As described earlier, the transducer is located at the distal end of the core. Therefore, the transducer's rotation rate within each rotation is variable in the same manner as the distal end of the core.

When the transducer is rotating at a rate less than what has been directed by the control apparatus due to whipping, sonic transmissions will occur more frequently within a given area than what has been directed by the control apparatus. That is, more than one transmission occurs per every 1.5° of transducer rotation. This results in that sector of the image displayed by the control apparatus being expanded. Likewise, when the transducer subassembly is rotating at a rate greater than what has been directed by the control apparatus, the corresponding sector of the displayed image will be compressed due to a less than accounted for transmission per degree rate. The end result is that an image is displayed having a fairly consistent but distorted image. While the image is fairly consistent due to rotational consistency, which is discussed later, it is nevertheless inaccurate and not a true depiction of the vasculature. This distortion of the angular mapping of the collected data is referred to as Non-Uniform Rotational Distortion (NURD).

Other intravascular imaging techniques such as Optical Coherence Tomography (OCT), are also susceptible to NURD. In OCT systems, image depth scanning is accomplished by varying the path length of a reference light beam. More image data collections per core rotation may be performed by an OCT than with a sonic imaging system. In spite of these characteristics, OCT is nevertheless susceptible to NURD.

Structurally, it is difficult and expensive to reliably manufacture a low NURD core. Therefore, attempts to correct or compensate for NURD in alternative manners have been made. For the most part, these attempts have involved the use of reflectors disposed within the sheath of the imaging catheter or spline shaped sheath cross-sections. In theory, the transducer would detect the reflectors or spline shapes of the sheath, and thereby be able to correct for NURD. However, in both cases, the resulting image is distorted. Now, instead of NURD, the images have been distorted by irregularities of the sheath wall or reflectors disposed within the sheath. NURD has been exchanged for an obstructed view which is only alleviated by the reduction in reflectors or the irregularity of sheath wall shape. Furthermore, in the case of irregularly shaped sheath walls, effective extrusion is very difficult, if not impossible, to achieve.

Therefore, a need exists in the art for an apparatus and method in which the NURD resulting from the whipping of rotating core assemblies can be significantly reduced if not eliminated altogether. It is desirable that this need be met in a manner which does not result in alternative distortions.

SUMMARY OF THE INVENTION

The present invention provides a method of determining the angular position of a sensor within a catheter having a sheath wall of varying thickness. The sensor is rotated and a center frequency emitted toward the sheath wall in order to obtain echoes which may be converted into thickness data to establish the angular position. A method of imaging is also provided.

An apparatus is provided with a rotatable core having a sensor. The core is located within a sheath having a wall of varying thickness.

BRIEF DESCRIPTION OF THE DRAWINGS

FIG. 5 is a table listing calculated values of the sheath wall thickness in conjunction with a "cos*" function.

FIG. 6 is a table listing calculated values of the "cos*" function, its standard deviation from the extremes of FIG. 5, its estimated standard error, and an angle A accounting for tolerance variations.

DETAILED DESCRIPTION OF THE INVENTION

Figure 1:
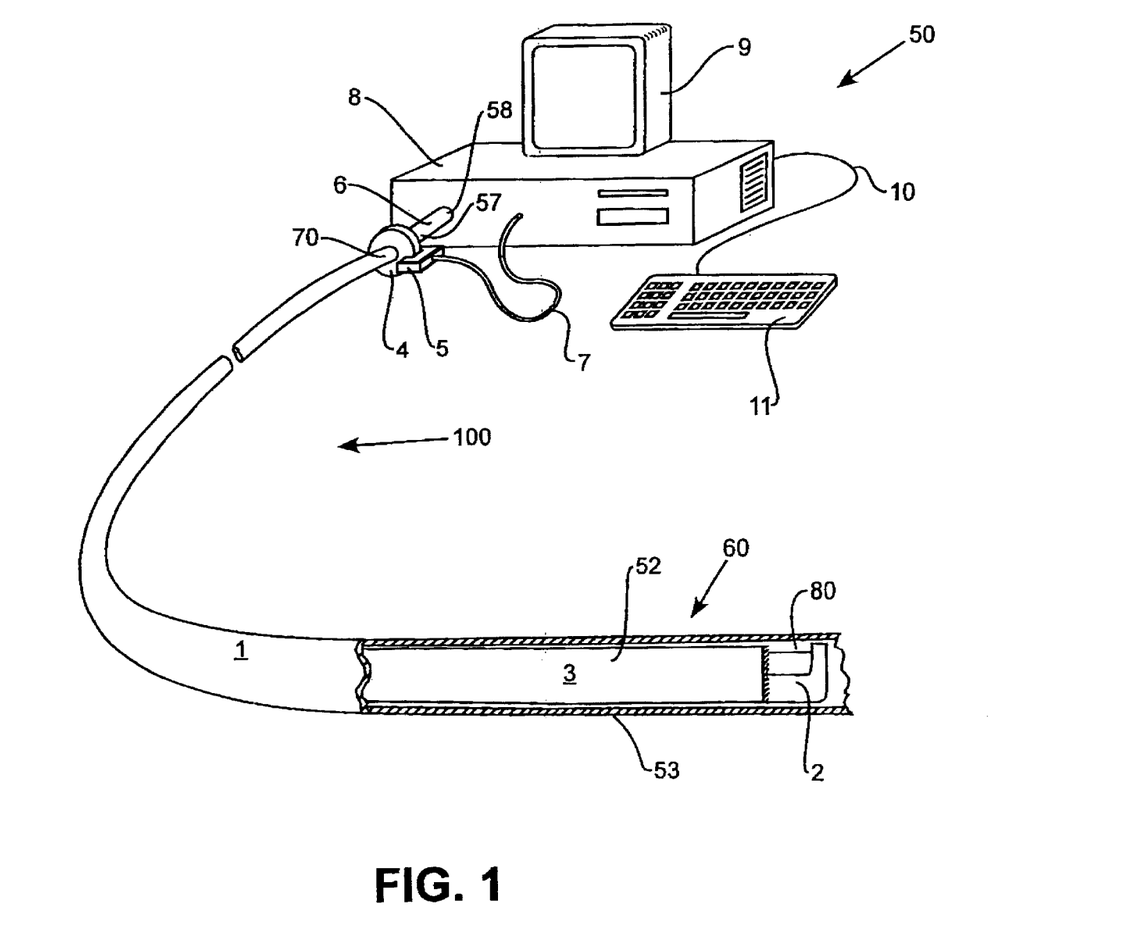
FIG. 1 is a perspective view of a mechanically driven imaging apparatus.
Figure 2:
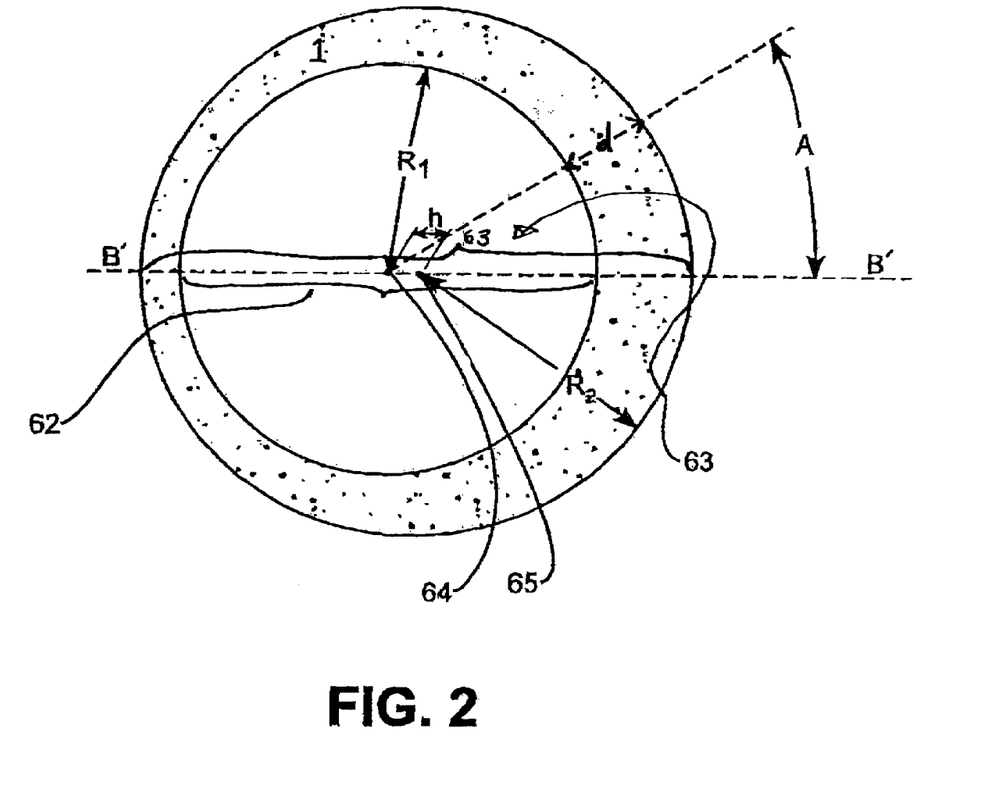
FIG. 2 is a sectional view of a sheath revealing an I.D. and an O.D. having separate offset centers.

Referring to FIGS. 1 and 2 an embodiment of the present invention is shown with a mechanically driven imaging apparatus 50. The imaging apparatus 50 consists of a longitudinal sheath 1 having a lumen 80 with a core 3 disposed therein. The core 3 has a distal end 52 with a sensor 2 disposed thereon. The sensor 2 is any device that collects image data (i.e. a lens, prism, mirror, transducer, or other such device). The sensor 2 is also surrounded by the longitudinal sheath 1 and is capable of longitudinal movement therein. The longitudinal sheath 1 has a sheath wall 53 of varying thickness. The thickness of the sheath wall 53 varies radially. The sensor 2 is capable of providing thickness data which is indicative of wall thickness d at varying locations.

Continuing with reference to FIG. 1, the core 3 has a proximal end (not shown) attached to a code wheel 4 at the terminal end 57 of an electromechanical shaft 6. A control apparatus 8 drives a proximal end 58 of the electromechanical shaft 6 at a predetermined constant rate of motion (i.e. 1,800 RPM). The sensor 2 delivers data relating to the catheter distal end 60 of the catheter 100 to the control apparatus 8 via the core 3 and electromechanical shaft 6. The control apparatus 8 receives data regarding the catheter proximal end 70 via an electrical cable 7 which runs between the control apparatus 8 and an optical detector 5 which is coupled to, and capable of detecting angular position readings regarding, the optical code wheel 4.

Continuing with reference to FIG. 1, a keyboard 11 is shown which communicates with the control apparatus 8 via a keyboard cable 10. The keyboard 11 allows the operator to set operational parameters, input data, manipulate images displayed on a monitor 9, and perform various other operations.

Referring to FIG. 2, a sectional view of a sheath 1 is shown. The sheath 1 has an I.D. 62 with corresponding I.D. center 64 and an O.D. 63 with corresponding O.D. center 65. The centers (64, 65) are offset from one another while both the I.D. 62 and the O.D. 63 are inner and outer diameters of the sheath 1. A circular inner surface of the sheath 1 corresponding to the I.D. 62 allows for smooth rotation of the core 3 (see FIG. 1). The circularity of the outer surface of the sheath 1 allows the sheath 1 to be inserted through vasculature with as little trauma and damage thereto as possible. However, circular inner and outer sheath 1 surfaces are not required. Rather oval or other irregular shapes may also be used, wherein the I.D. 62 and the O.D. 63 actually reference measurements which are not true diameters (i.e. were the sheath 1 surfaces not truly circular perimeters). The embodiments of FIGS. 1–6 and equations 1–5 (which follow) are described with reference to true circular sheath 1 surfaces. However, alternative shapes may be used.

Plastic tubing extrusion dies can easily be adjusted to extrude this type of intentionally variable cross-sectional sheath 1. This helps keep the cost of the present invention very low. In fact, it is difficult, if not impossible, to extrude a plastic tube without this type of cross-section to some degree. Additionally, greater dimensional control is available by way of conventional "hot die", molding or other techniques. These techniques can easily be adapted to provide a more consistent, lower tolerance cross-section of this configuration with only a modest increase in cost.

The I.D. radius $R_1$ and the O.D. radius $R_2$ are shown. A distance h is shown between the I.D. center 64 and the O.D. center 65. For reference, line B'—B' is shown as a horizontal axis through both the I.D. center 64 and the O.D. center 65 as positioned. Noting that sensor 2 (see FIG. 1) would be centered at the I.D. center 64, a hypothetical counterclockwise rotation from 0° (at line B'—B') has occurred to create an angle A wherein a wall thickness d is shown. As the sensor 2 rotates it detects the wall thickness d in precise locations. The control apparatus 8 is able to determine the wall thickness d. Because the wall thickness d changes are fairly gradual there is little distortion due to refraction.

A typical sheath 1 for a coronary imaging catheter has a fairly uniform wall thickness d of about 0.004". For overall size and flexibility purposes, it may be desirable that the sheath 1 of the present invention have at least the thinnest portion of its wall thickness d not exceed 0.004" to any significant degree (i.e. beyond 0.006"). Depending on the sheath material chosen, a minimum wall thickness d between 0.001" and 0.006" should suffice. For example, if the sensor is an OCT device, with a resolution typically about 0.001" or less, then detecting such a wall thickness d is attainable. Alternatively, if the sensor 2 is ultrasonic, having an axial resolution typically about 0.004" or larger, then the wall thickness d in this area should exceed 0.004" unless other means are employed to improve axial resolution.

Figure 3:
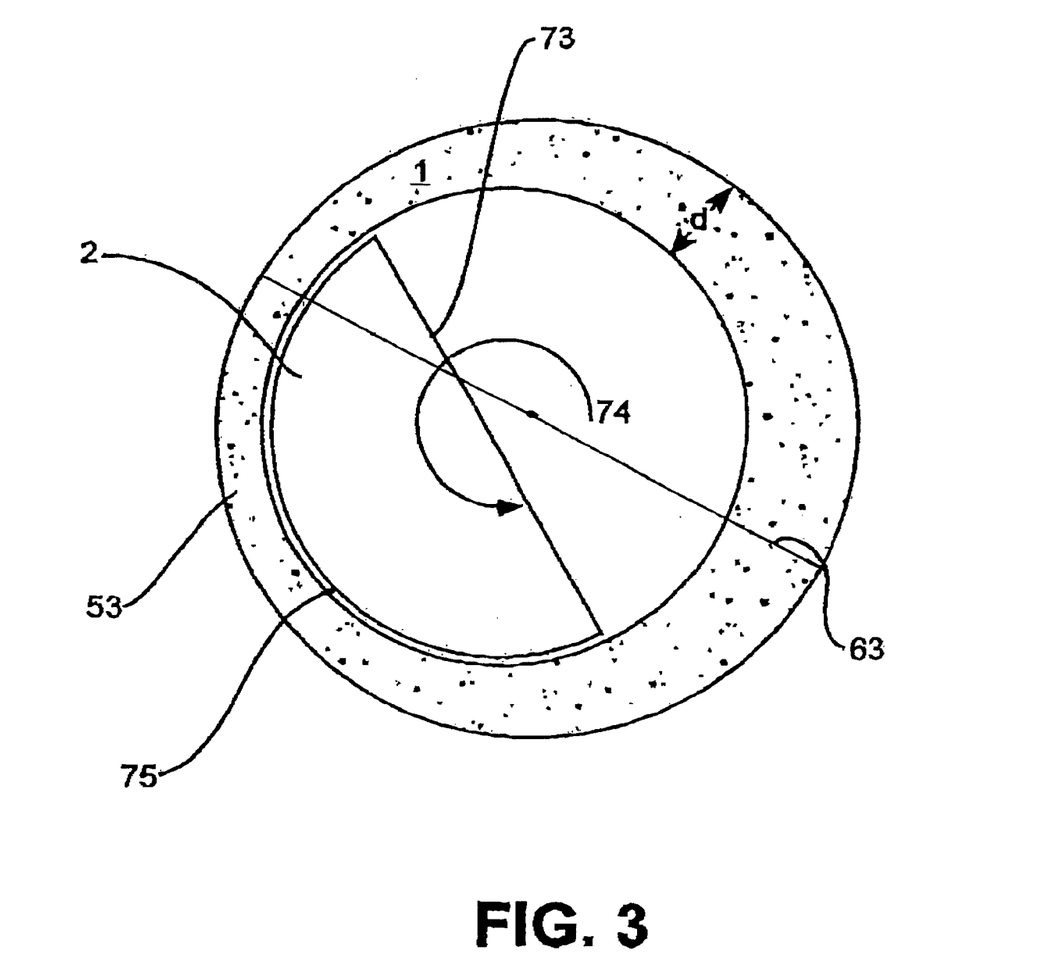
FIG. 3 is a sectional view of a sheath with a sensor rotably mounted therein.

Referring to FIGS. 1–3, an embodiment of the sensor 2 of the present invention is able to determine wall thickness d, by providing thickness data, while retrieving image data of surrounding vasculature simultaneously. That is, a single transducer subassembly (i.e. sensor 2) may be operated at vessel and sheath imaging center frequencies which can be the same or different frequencies. If different, these frequencies may be generated and detected simultaneously, independently and without significant interference from one another. Thus, the cost and space requirements of an additional sensor 2 to image the sheath 1 is avoided.

Current high-end resolution ultrasonic transducer subassemblies, used to image vessels, operate in the 30 to 45 MHz center frequency range. The higher the center frequency, the better the axial resolution but the lower the depth to which tissue may be imaged (i.e. depth of penetration). The transducer subassembly generates and detects a peak amplitude sonic signal at a center frequency. The center frequency will have a wavelength four times the acoustic thickness of the piezoelectric material of the transducer. Additionally, peak sonic signals at progressively lower amplitudes may be generated and detected with increasing odd multiples (3, 5, 7, etc.) of this center frequency. That is, three, five, or seven times the center frequency may be generated and detected with the same transducer. Due to its lower depth of penetration and better axial resolution, the higher (i.e. multiplied) center frequency pulse is well suited to collect wall thickness data.

An ultrasonic transducer subassembly (i.e. sensor 2) can be operated at, at least, 3 times its center frequency. For example, a 30 MHz center frequency sensor 2 may be operated at 90 MHz center frequency. At 90 MHz, the axial resolution of the sensor 2 would typically be less than 0.002". This is adequate to reliably detect a wall thickness d near 0.004". The sheath wall 53 is in fluid communication with the sensor 2 and generally would not be less than 0.002" to any large degree. Therefore, there is adequate depth of penetration and axial resolution to image the sheath 1 at these higher frequencies (i.e. 90 MHz).

The present invention anticipates data collection by the sensor 2 at very small angular increments (i.e. every 0.3°) of the proximal end of the core (not shown). Vessel image data is not normally collected at such small angular intervals in the prior art because there would be no discernable improvement in the displayed vessel image. However, in the present invention, additional image data may be used to produce an image with or without a reduced degradation of lateral resolution where the distal end of the core 52 is rotating at a rate greater than directed by the control apparatus 8 (see also FIG. 1).

Echoes that are strong enough to be displayed may be received from vessel structures as far as 20 mm (depth of penetration) from a 30 MHz center frequency sensor 2. The speed of sound in tissues is about 1500 Meter/sec. These numbers indicate that image data collection could occur at approximately 0.027 milliseconds after the initial transmission of a sonic pulse. That is, this is the amount of time it takes the generated pulse to travel to vessel structures (20 mm) and return (20 mm) when traveling at about 1500 Meter/sec. Assuming a rotation rate of 1800 RPM, this is approximately every 0.3° or five (5) times more often than the conventional rate discussed in the background section here. The present invention benefits from a higher rate of collection without the interference of echoes generated from a previously transmitted sonic pulse. If the sensor is operated at higher frequencies, independent of lower frequency image data collections, the rate of data collection may be greater due to a lower depth of penetration.

Referring to FIGS. 1–3, in order to eliminate NURD, imaging data can be made dependent upon the determination of wall thickness d. That is, readings concerning the angle A are susceptible to NURD because they are directed and retrieved at the proximal end (not shown) of the core 3, before NURD has occurred, via an electromechanical shaft 6 and code wheel 4 respectively. However, wall thickness d is determined at the distal end 52 of the core 3, after the effects of NURD have occurred (discussed further herein). Therefore, instead of merely relying upon proximal indicators of the angle A, such as the electromechanical shaft 6 and code wheel 4, the present invention allows us to know the true angle A as determined based upon the distal indicator of wall thickness d. Knowing the true angle A accounts for NURD. This knowledge allows an adjustment for the effects of NURD. The adjustment eliminates compressed and expanded images on the monitor 9. These distorted images would otherwise result if it is simply assumed that a certain amount of core 3 rotation at the core proximal end (not shown) equates to the same amount of rotation at the distal end 52.

Referring to FIGS. 2 and 3, as stated above, the present invention allows us to know the true angle A as determined based upon the distal indicator of wall thickness d. That is, the wall thickness d is related to angle A as indicated in the following Equation:

$$d = h\cos(A) - R_1 + \sqrt{R_2^2 + h^2 \sin^2(A)} \qquad \text{Equation 1}$$

The sensor 2 is collecting data to allow the control apparatus 8 to determine real time wall thickness d values. Meanwhile values for the I.D. radius $R_1$, the O.D. radius $R_2$, and the distance h between the I.D. center 64 and the O.D. center 65 may be predetermined and compiled into a predetermined angular data thickness set. This leaves only the remaining variable of angle A to be determined. The angle A can be determined by comparison to the predetermined angular data thickness set. Determining a value for the angle A in this manner accounts for the NURD which occurs when the angle A is merely assumed based on values assigned, mechanically acted upon, and retrieved only at the core proximal end (not shown). However, as discussed later, an even more sophisticated approach may be desired to eliminate other distortion.

Referring to FIG. 3, a sectional view of the sheath 1 with a sensor 2 rotably mounted therein is shown. The sensor 2 may be of any type capable of detecting wall thickness d. The sensor 2 is shown with a flat detection surface 73 running parallel to and within the sheath 1. However, it is not essential that the flat detection surface 73 be positioned in this manner. An arrow 74 indicates the direction of rotation of the sensor 2 for purposes of the descriptions here. However, there is no requirement that the sensor 2 rotate in one direction over another. Additionally, the sensor 2 is shown having a rounded cooperating surface 75. While the shape of the rounded cooperating surface 75 helps facilitate rotation of the sensor 2 within the sheath, it is not essential that the rounded cooperating surface 75 be shaped or positioned as shown.

Figure 4:
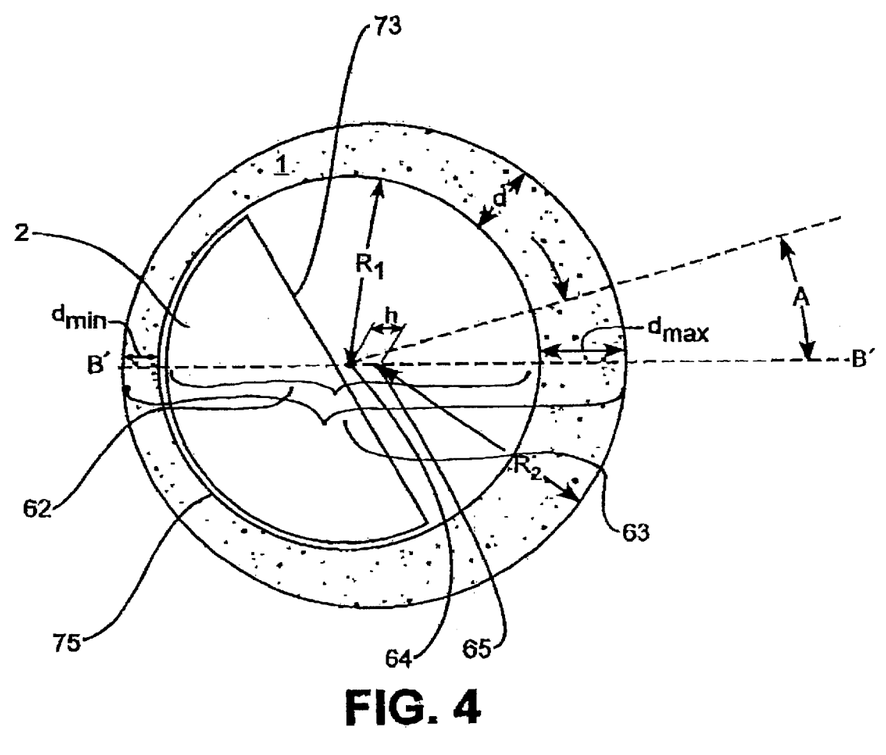
FIG. 4 is a sectional view of a sheath revealing centers and a sensor.

Referring to FIG. 4, a sectional view of an embodiment of the sheath 1 is shown. The I.D. center 64, O.D. center 65, and sensor 2 are shown. The sensor 2 rests within the I.D. 62 and therefore rotates about the I.D. center 64. It is the sensor 2 rotation about the I.D. center 64 which allows angle A to be determined. That is, it is the sensor 2 which actually allows the determination of wall thickness d data, but it is the I.D. radius $R_1$ (and thus the position of the I.D. center 64) which is actually known. Because the sensor 2 and the I.D. 62 share the I.D. center 64, angle A can be determined.

Referring to FIGS. 1 and 4, NURD can be effectively eliminated by knowing the true value of angle A. For example, even though whipping may result in non-uniform rotation of the core 3 at its distal end 52, knowing the true angle A allows mapping of image data based on the true angle A as opposed to mere blind reliance on the angular position of the core proximal end (not shown).

Referring to FIGS. 1 and 4, data collection based on knowledge of the true position of the sensor 2 may proceed in various manners. For example, where whipping has resulted in insufficient data collection over a given portion of sensor 2 rotation (i.e. because the sensor 2 rotated quicker than directed), sufficient additional data may be provided. The additional data may be provided by collecting image data more rapidly and/or interpolated from the data which has been accumulated. Conversely, if too much data has been accumulated over a given portion of sensor 2 rotation (i.e. because the sensor 2 rotated slower than directed), the additional data may be interpolated, averaged, or judiciously discarded. Such accounting of data and resultant interpolations may occur in partial or complete intervals of rotation as it is only within the individual rotation that significant effects of whipping are seen. The pattern of the whipping changes very slowly from rotation to rotation. Rotation rate (i.e. rotational velocity), as measured in complete intervals, changes minimally from rotation to rotation. Thus, images and/or data may be averaged at an average rotation rate interval over several rotation intervals. This may provide increased immunity to noise, the ability to predict the current angle A in advance of a data collection and/or reduce the effects of sheath wall 53 imperfections on the determination of angle A. These and potentially other data collection methods may proceed in a manner which eliminates NURD once the true angle A, and sensor 2 position have been determined.

Referring to FIG. 5 a table referencing an embodiment of the present invention is shown listing the calculated values of wall thickness d in conjunction with a "cos*" function explained further here. This table lists the computed wall thickness d values for a typical sheath 1 at 10 degree increments of angle A. The sheath 1 specifications for purposes of this example include an O.D. 63 of 0.045"±0.001" ($R_2$=0.0225"±0.0005"), an I.D. 62 of 0.033"±0.001" ($R_1$=0.0165"±0.0005"), and a distance h of 0.002"+0.001". These tolerances are typical of a tube extruded under fairly controlled conditions. The values are referenced within the table of FIG. 5. It should be noted that these values are merely exemplary and should not be interpreted as limiting of the invention or its particular dimensions or other measurements. For reference, an additional FIG. 6 is provided listing calculated values of the cos* function of FIG. 5 in relation to a standard deviation, standard error, and angle A, accounting for tolerance variations.

With continuing reference to FIG. 5, solving for cos(A) provides:

$$\cos(A) = \frac{d + R_1 - \sqrt{R_2^2 - h^2\sin^2(A)}}{h} \quad \text{Equation 2}$$

The term "$h^2\sin^2(A)$" of this equation is fairly negligible. Therefore, for purposes explained further below, the term "$h^2\sin^2(A)$" has been deleted resulting in the following Equation 3 is provided wherein cos*(A) is given as:

$$\cos^*(A) = \frac{d + R_1 - R_2}{h} \quad \text{Equation 3}$$

Ultimately, elimination of the term "$h^2\sin^2(A)$" will result in an estimated maximum standard error of no greater than about 0.1 degrees in determination of angle A, whereas its removal allows for Equation 6, which is shown and described further below.

In addition to the above referenced values, FIG. 4 also points out a maximum wall thickness value $d_{max}$ and a minimum wall thickness value $d_{min}$. While a good indicator of the angle A, and thereby position of the sensor 2, wall thickness d should be understood in light of dimensional variations of the sheath 1. Examples of these dimensional variations are found in the eight columns of FIG. 5 labeled "Dimensional Extremes". Wall thickness d, the I.D. radius $R_1$, the O.D. radius $R_2$, and distance h are all variables subject to manufacturing tolerances. As a result, the mere assumption that a particular wall thickness d is indicative of a particular angle A (and therefore sensor 2 position) may not always be entirely accurate. That is, the benefit of Equation 1 which allows an accounting for of NURD may allow other distortion to occur due to the imperfections of catheter manufacturing. For example, the sheath 1 may have certain non-uniformities due to particular flow properties of its plastic composition, extruder parameters, or die design. Fortunately, the present invention allows for an accounting of such tolerance variations. While potentially valuable (i.e. for the perfectly manufactured catheter), it is not necessary to rely on predetermined values for the I.D. radius, the O.D. radius, and distance h. Rather, actual wall thickness d determinations are constantly being made which could be utilized. Once a complete revolution of the sensor 2 has occurred a maximum wall thickness value $d_{max}$ and a minimum wall thickness value $d_{min}$ may be determined (see also FIG. 4). As shown by the following Equations 4, 5, and 6, knowing the actual maximum wall thickness $d_{max}$ and a minimum wall thickness $d_{min}$ values allows the replacement of the more uncertain variables for distance h, the I.D. radius $R_1$, and the O.D. radius $R_2$ when determining the angle A via cos*(A). Consider:

$$h = \frac{d_{max} - d_{min}}{2} \quad \text{Equation 4}$$

And, $$R_1 - R_2 = -\frac{d_{max} + d_{min}}{2}, \quad \text{Equation 5}$$

Therefore . . .

$$\cos^*(A) = \frac{d - \frac{d_{max} + d_{min}}{2}}{\frac{d_{max} - d_{min}}{2}}$$

Or in other words . . .

$$\cos^*(A) = \frac{2d - d_{max} - d_{min}}{d_{max} - d_{min}} \quad \text{Equation 6}$$

Given the above Equation 6, dimension variances become much less significant. The measurable variables for wall thickness d, maximum wall thickness $d_{max}$ and a minimum wall thickness $d_{min}$ can all be precisely determined with data collected by the sensor 2 in order to give exact values for cos*(A). We can now determine the angle A and account for the true position of the sensor 2 within its rotation from a thickness data set in the form of a look up table.

Equations 1–6 may be used to determine angle A, as indicated. These equations may be processed as an algorithm by a computer of the control apparatus 8 (see FIG. 1).

Referring to FIG. 6, a look up table referencing an embodiment of the present invention may display a cos* value for a given set of values for the I.D. radius $R_1$, the O.D. radius $R_2$, and the distance h. Angle A is determined with an estimated maximum standard error of less than 1.3 degrees. To further reduce the maximum standard error two look up tables may be created, one for the high end of the tolerance range of the distance h and one for the low end. A third look up table may be created from these first two look up tables using standard interpolation techniques. Values for the third look up table would be adjusted if the values for the distance h were different between the tables. This technique would result in an estimated maximum standard error of about 0.1 degrees.

Lastly, with reference to FIGS. 1 and 4, an additional step may be taken to ensure improved accuracy of the results. In order to ensure the positioning of the sensor 2 within the sheath 1 as determined by angle A measurements, it may be desirable to collect data first on a test set-up. The test set-up would involve placing a sensor 2 within actual samples of the sheath 1. The core 3 would be replaced with a short and stiff sheath (not shown) to ensure positioning of the sensor 2 within the sheath 1 and eliminate NURD. The test set-up would be used to determine look-up table values of cos*(A)

or wall thickness d for later comparison to results obtained during use of the imaging apparatus 50. The look-up table values could be used to ensure the accuracy of results.

Whether a test set-up is created or not, Equation 6 allows the elimination of distortion due to NURD and catheter manufacturing imperfections. As a result, NURD may be eliminated in an effective, accurate, and cost conscious manner.

Although an exemplary embodiment of the invention has been shown and described in the form of a particular IVUS catheter, many changes, modifications, and substitutions may be made without departing from the spirit and scope of this invention. Such modifications and extensions are anticipated and included here.

I claim:

1. A method of determining the angular position of a sensor within a catheter wherein said method comprises:
    rotating said sensor;
    emitting a first center frequency from said sensor toward a sheath wall of varying thickness of said catheter;
    retrieving wall echoes of said first center frequency with said sensor from said sheath wall of varying thickness; and,
    converting said wall echoes into thickness data, said thickness data indicative of an angular position of said sensor within said catheter.

2. The method of claim 1 further comprising:
    placing said catheter within a vessel prior to said rotating;
    releasing a second center frequency from said sensor toward said vessel after said rotating, said second center frequency being lower than said first center frequency;
    receiving vessel echoes of said second center frequency with said sensor from said vessel;
    translating said vessel echoes into image data; and,
    correlating said image data to said thickness data following said converting.

3. The method of claim 1 wherein said sheath wall of varying thickness varies in thickness circumferentially in a gradual manner.

4. The method of claim 1 wherein said sheath wall of varying thickness varies in thickness circumferentially to allow said thickness data to be indicative of said angular position.

5. The method of claim 4 further comprising associating said thickness data with a predetermined angular data thickness set after said converting in order to indicate the angular position of said sensor within said catheter.

6. The method of claim 1 further comprising establishing a minimum wall thickness and a maximum wall thickness of said sheath wall of varying thickness, said thickness data being an actual thickness data set after said converting due to said minimum wall thickness and said maximum wall thickness.

7. The method of claim 1 further comprising:
    accounting for an amount of said thickness data in partial intervals of rotation during said rotating; and,
    providing any necessary adjustment to said thickness data based on said amount to ensure the angular position of said sensor within said catheter.

8. The method of claim 1 further comprising:
    accounting for an amount of said thickness data in complete intervals of rotation during said rotating; and,
    providing any necessary adjustment to said thickness data based on said amount to ensure the angular position of said sensor within said catheter.

9. The method of claim 1 wherein said retrieving occurs within at least every 0.3 degrees of said rotating.

10. The method of claim 1 wherein said rotating includes rotating said sensor in a circular manner.

11. The method of claim 2 wherein said second center frequency is 30 MHz.

12. The method of claim 1 further comprising storing said thickness data as test set-up information after said converting.

13. The method of claim 1 wherein said sensor is an intravascular ultrasound sensor.

14. The method of claim 1 wherein said sensor is an optical coherence tomography sensor.

15. The method of claim 2 wherein said emitting, said retrieving, said releasing, and said receiving occur simultaneously, said sensor comprising a single sensor.

16. The method of claim 2 wherein said first center frequency is an odd multiple of said second center frequency.

17. The method of claim 2 wherein said first center frequency is 90 MHz.

18. The method of claim 2 further comprising:
    establishing a minimum wall thickness and a maximum wall thickness of said sheath wall of varying thickness, said thickness data being an actual thickness data set after said converting due to said minimum wall thickness and said maximum wall thickness;
    accounting for an amount of said thickness data in intervals of rotation during said rotating; and,
    providing any necessary adjustment to said thickness data based on said amount to ensure the angular position of said sensor within said catheter.

19. The method of claim 18 wherein said rotating, said emitting, said retrieving, said converting, said releasing, said receiving, said translating, said correlating, said displaying, said establishing, said accounting, and said providing occur simultaneously.

20. A method of imaging a vessel comprising:
    placing a catheter with a sensor in said vessel;
    rotating said sensor;
    emitting a first center frequency from said sensor toward a sheath wall of varying thickness of said catheter;
    retrieving wall echoes of said first center frequency with said sensor from said sheath wall of varying thickness;
    converting said wall echoes into thickness data, said thickness data indicative of an angular position of said sensor within said catheter;
    releasing a second center frequency from said sensor toward said vessel after said rotating, said second center frequency being lower than said first center frequency;
    receiving vessel echoes of said second center frequency with said sensor from said vessel;
    translating said vessel echoes into image data;
    correlating said image data to said thickness data following said converting; and,
    displaying an image of said vessel based upon a correlation resulting form said correlating.

21. A medical device apparatus comprising:
    a core having a distal end and a proximal end, said core being rotatable;
    a sensor attached to said core at said distal end;
    a control apparatus in communication with said core at said proximal end; and, a sheath surrounding said core, said sheath having a sheath wall of a designed varying thickness.

22. The apparatus of claim 21 further comprising:

a flat detection surface of said sensor, said flat detection surface running parallel to and facing said sheath wall of varying thickness; and, a rounded cooperating surface of said sensor, said rounded cooperating surface opposite said flat detection surface.

23. The apparatus of claim 21 further comprising a monitor in communication with said control apparatus, said monitor capable of displaying an image of vasculature surrounding said sheath when said sheath is present therein.

24. The apparatus of claim 21 further comprising a keyboard in communication with said control apparatus, said keyboard capable of directing operational parameters when using said apparatus.

25. The control apparatus of claim 21 further comprising means for determining the position of said sensor within said sheath.

26. The apparatus of claim 25 wherein said position is determined by said control apparatus based upon thickness data obtained by said sensor from said sheath wall, said thickness data evaluated by a computer of said control apparatus in light of a predetermined algorithm.

27. The apparatus of claim 21 further comprising;

an inner diameter of said sheath, said inner diameter having an inner diameter center; and, an outer diameter of said sheath, said outer diameter having an outer diameter center, said inner diameter center being offset from said outer diameter center.

28. The apparatus of claim 21 further comprising a minimum wall thickness of said sheath wall of varying thickness, said minimum wall thickness not exceeding 0.006 inches in thickness.

29. The sheath wall of varying thickness of claim 28 wherein said minimum wall thickness is at least 0.001 inches in thickness.

30. The apparatus of claim 21 further comprising an electromechanical shaft between said control apparatus and said core, said electromechanical shaft capable of rotating said core.

31. The apparatus of claim 30 further comprising:

a code wheel surrounding said electromechanical shaft; and an optical detector in communication with said code wheel and capable of providing data regarding said electromechanical shaft to said control apparatus via an electric cable there between.

32. The apparatus of claim 21, wherein said designed varying thickness indicates an angular position of said sensor.

* * * * *

UNITED STATES PATENT AND TRADEMARK OFFICE
CERTIFICATE OF CORRECTION

PATENT NO. : 6,450,964 B1 Page 1 of 1
DATED : September 17, 2002
INVENTOR(S) : Webler It is certified that error appears in the above-identified patent and that said Letters Patent is hereby corrected as shown below:

Title page,
Item [75], Inventor, please delete "Newark, CA" and insert -- Escondido, CA --.
Item [56], References Cited, U.S. PATENT DOCUMENTS, please delete "Shakhovich" and insert -- Shaknovich --.
OTHER PUBLICATIONS, before the word "headings" please insert -- Subj. --.
Above item [74], *Attorney, Agent or Firm*, in the *Assistant Examiner*, please delete "Manlin" and insert -- Maulin --.

Signed and Sealed this

Twenty-third Day of March, 2004

JON W. DUDAS
*Acting Director of the United States Patent and Trademark Office*